United States Patent
Fenner et al.

[11] Patent Number: 6,052,623
[45] Date of Patent: Apr. 18, 2000

[54] FEEDTHROUGH ASSEMBLY FOR IMPLANTABLE MEDICAL DEVICES AND METHODS FOR PROVIDING SAME

[75] Inventors: Andreas A. Fenner, Chandler; Lary R. Larson, Gold Canyon, both of Ariz.; Daniel R. Greeninger, Coon Rapids; David L. Thompson, Fridley, both of Minn.

[73] Assignee: Medtronic, Inc., Minneapolis, Minn.

[21] Appl. No.: 09/201,059

[22] Filed: Nov. 30, 1998

[51] Int. Cl.[7] .................................................. A61N 1/375
[52] U.S. Cl. .......................................................... 607/36
[58] Field of Search .................................. 607/2, 36, 37

[56] References Cited

U.S. PATENT DOCUMENTS

| | | |
|---|---|---|
| 4,678,868 | 7/1987 | Kraska . |
| 4,750,495 | 6/1988 | Moore et al. . |
| 4,821,723 | 4/1989 | Baker et al. . |
| 5,131,388 | 7/1992 | Pless . |
| 5,144,949 | 9/1992 | Olsen et al. . |
| 5,158,078 | 10/1992 | Bennett et al. . |
| 5,199,428 | 4/1993 | Obel et al. . |
| 5,207,218 | 5/1993 | Carpentier et al. . |
| 5,312,453 | 5/1994 | Shelton et al. . |
| 5,314,430 | 5/1994 | Bardy . |
| 5,330,507 | 7/1994 | Schwartz . |
| 5,331,966 | 7/1994 | Bennett et al. . |
| 5,354,316 | 10/1994 | Keimel . |
| 5,545,186 | 8/1996 | Olson et al. . |
| 5,649,965 | 7/1997 | Pons et al. . |
| 5,735,884 | 4/1998 | Thompson et al. . |

*Primary Examiner*—William E. Kamm
*Attorney, Agent, or Firm*—Thomas F. Woods; Harold R. Patton

[57] ABSTRACT

A feedthrough assembly for an implantable medical device includes one or more electrically conductive pins extending through apertures in a case of the medical device with the electrically conductive pins being insulated from the case. The feedthrough assembly further includes a printed circuit board having a diode protection circuit mounted thereon. The printed circuit board forms at least a part of electrically conductive paths for connection of the electrically conductive pins to a medical device circuit assembly mounted within the case. The printed circuit board further provides for electrical connection of the diode protection circuit mounted thereon between the electrically conductive pins and the case.

29 Claims, 5 Drawing Sheets

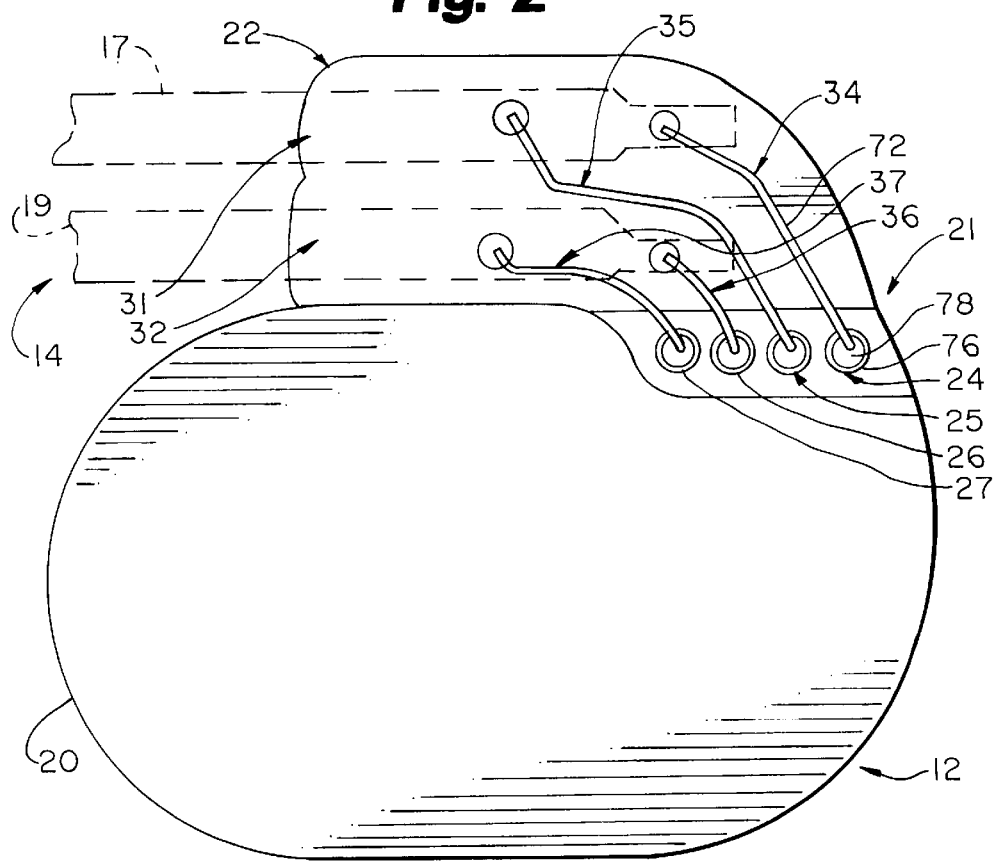
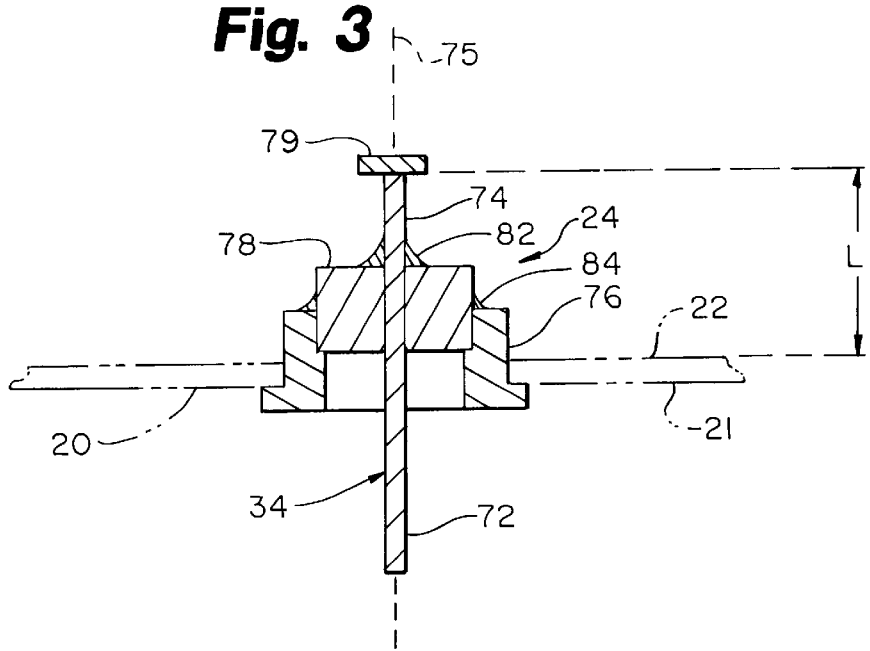

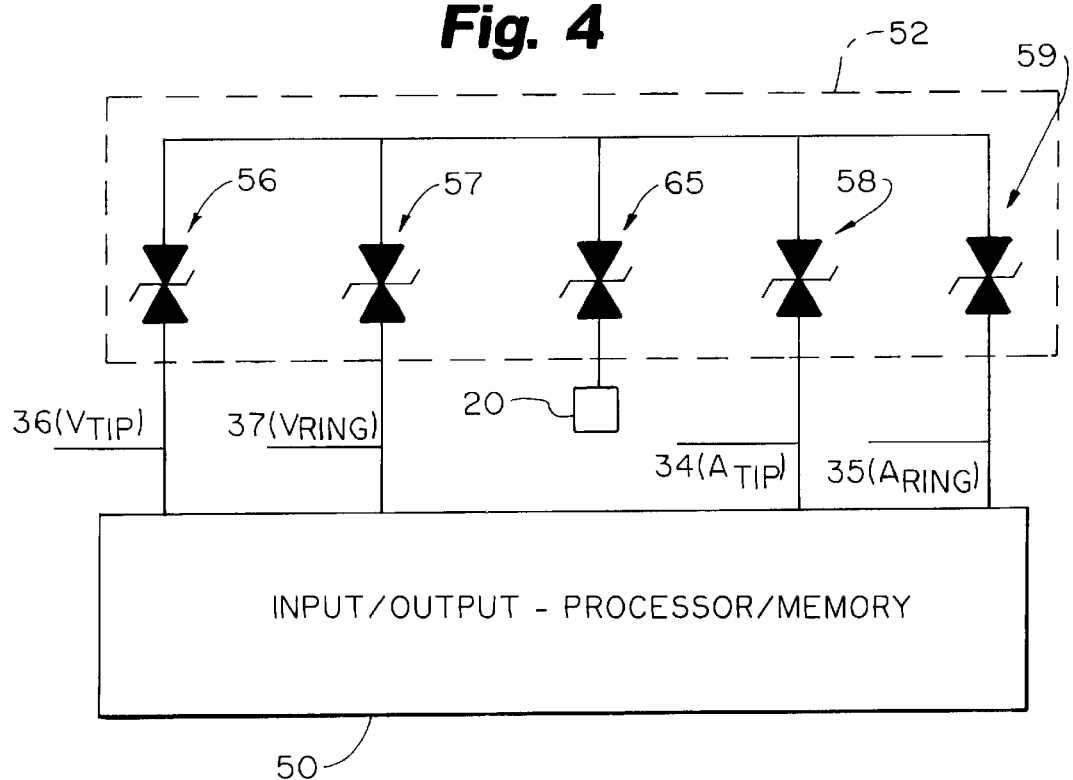
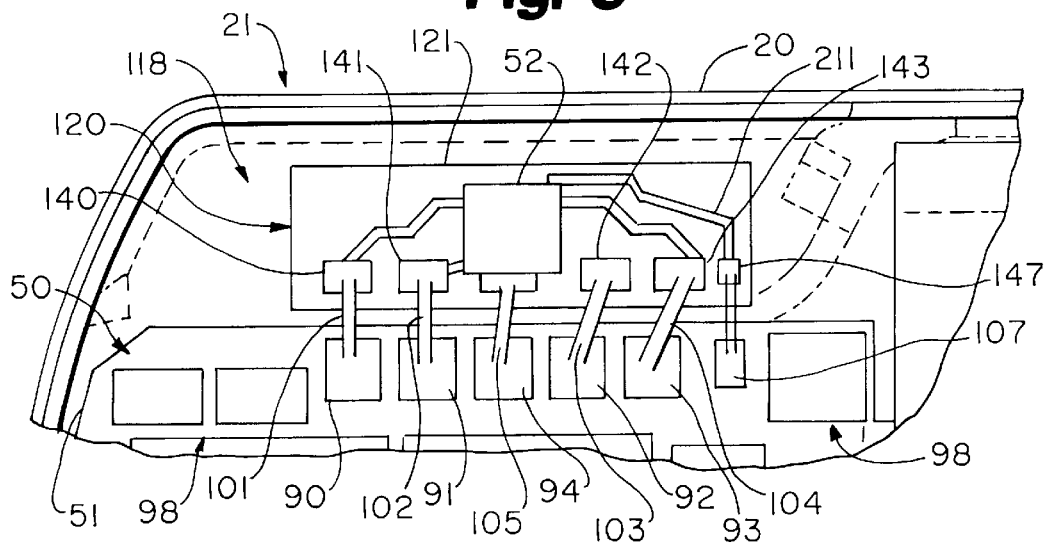

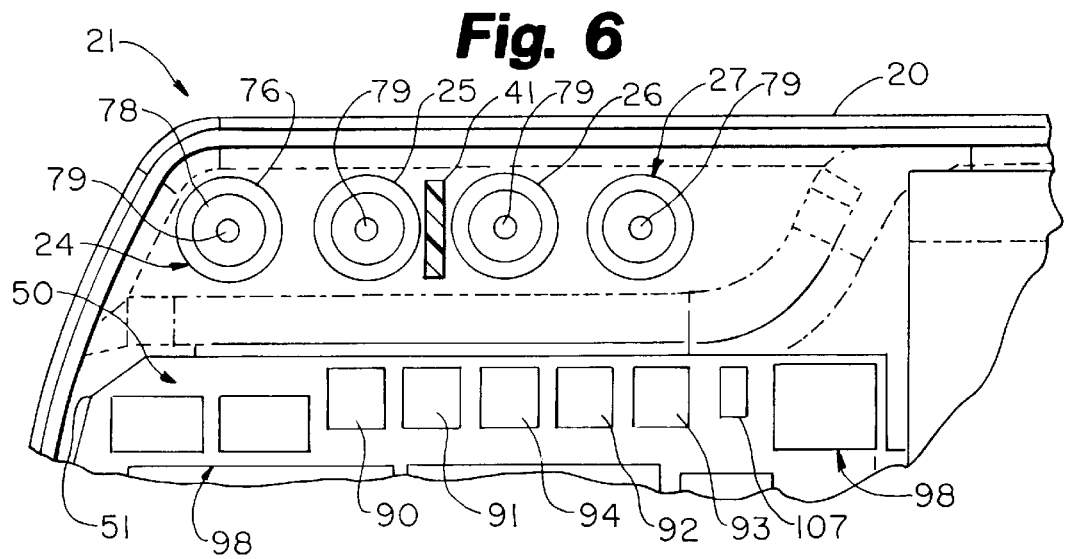
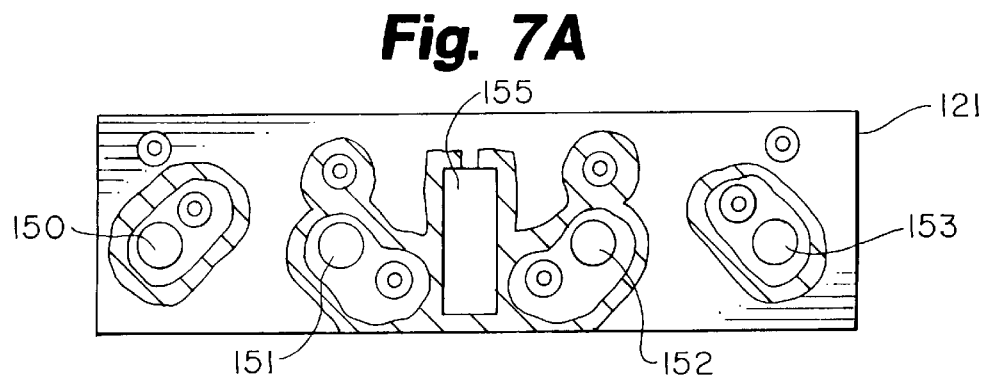
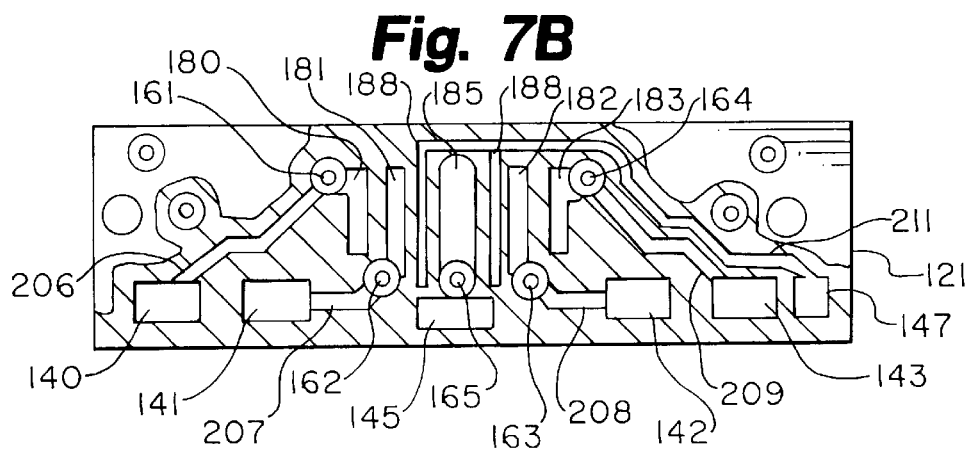

FEEDTHROUGH ASSEMBLY FOR IMPLANTABLE MEDICAL DEVICES AND METHODS FOR PROVIDING SAME

FIELD OF THE INVENTION

The present invention relates to medical devices, e.g., implantable medical devices. More particularly, the present invention pertains to feedthroughs for sealed electrical connections which provide for protection against electrical interference for such medical devices.

BACKGROUND OF THE INVENTION

Implantable medical devices typically have a metal case and a connector block mounted to the metal case which includes receptacles for leads which may be used for electrical stimulation or which may be used for sensing of physiological signals. Hermetically sealed within the case are the battery and the circuitry associated with the particular medical device, e.g., pacemaker circuitry, defibrillator circuitry, etc. Electrical feedthroughs are employed to connect the leads outside the metal case with the medical device circuitry and the battery inside the metal case.

Electrical feedthroughs serve the purpose of providing an electrical circuit path extending from the interior of a hermetically sealed metal case to an external point outside the case while maintaining the hermetic seal of the case. A conductive path is provided through the feedthrough by a conductive pin which is electrically insulated from the case itself. Such feedthroughs typically include a ferrule which permits attachment of the feedthrough to the case, the conductive pin, and a hermetic glass or ceramic seal which supports the pin within the ferrule and isolates the pin from the metal case. For example, illustrative feedthroughs are shown in U.S. Pat. No. 4,678,868 issued to Kraska, et al. and entitled "Hermetic electrical feedthrough assembly," in which an alumina insulator provides hermetic sealing and electrical isolation of a niobium conductor pin from a metal case. Further, for example, a filtered feedthrough assembly for implantable medical devices is also shown in U.S. Pat. No. 5,735,884 issued to Thompson, et al. and entitled "Filtered Feedthrough Assembly For Implantable Medical Device," in which protection from electrical interference is provided using capacitors and zener diodes incorporated into a feedthrough assembly.

Implantable medical devices can, under some circumstances, be susceptible to electrical interference such that functioning of the medical device is impaired. For example, medical devices may require protection against electrical interference from electromagnetic interference (EMI), electrocautery pulses, defibrillation pulses, electrostatic discharge, or other generally large voltages or currents generated by other devices external to the medical device. Such electrical interference can damage the circuitry of such medical devices or cause interference in the proper operation or function of the medical device. For example, damage may occur due to high voltages or excessive currents introduced into the medical device circuitry, e.g., pacemaker circuitry. Therefore, it is required that such voltages and currents be limited at the input of such medical devices, e.g., at the feedthrough. Protection from such voltages and currents is typically provided at the input of a medical device by the use of one or more zener diodes and one or more filter capacitors. For example, one or more zener diodes may be connected between the circuitry to be protected, e.g., pacemaker circuitry, and the metal case of the medical device in a manner which grounds voltage surges and current surges through the diode(s).

Such zener diodes and capacitors used for such applications may be in the form of discrete components mounted relative to circuitry at the input of a connector block where various leads are connected to the implantable medical device, e.g., at the feedthroughs for such leads. However, such protection provided by zener diodes and capacitors placed at the input of the medical device increases the congestion of the medical device circuits, particularly due to the need to provide a relatively high number of such discrete components, e.g., at least one zener diode and one capacitor per input/output connection or feedthrough, of the medical device. This is contrary to the desire for increased miniaturization of implantable medical devices, particularly in complex devices such as multiple chamber pacemakers, defibrillators, etc.

Further, generally, when such protection is provided, interconnect wire length for connecting such protection circuitry and pins of the feedthroughs to the medical device circuitry which performs desired functions for the medical device tends to be undesirably long. Such excessive wire length may lead to signal loss and undesirable inductive effects. Further, the wire length can act as an antenna that radiates undesirable electrical interference signals to sensitive circuits within the medical device to be protected. In other words, the wire length can reradiate interfering signals due to high current flow through the interconnect wires. This causes voltages to be induced in the high impedance CMOS circuitry of the implanted medical device. For example, such induced voltages can cause false sensing (e.g., under and/or oversensing) or can upset circuit function (e.g., cause a power on reset for a circuit).

Table 1 below lists some U.S. patents that use zener diode protection techniques:

TABLE 1

| U.S. Pat. No. | Inventor(s) | Issue Date |
| --- | --- | --- |
| 5,735,884 | Thompson et al. | 7 April 1998 |
| 5,649,965 | Pons et al. | 22 July 1997 |
| 4,750,495 | Moore et al. | 14 June 1988 |

All patents listed in Table 1, and elsewhere herein, are incorporated by reference in their respective entireties. As those of ordinary skill in the art will appreciate readily upon reading the Summary of the Invention, Detailed Description of the Embodiments, and claims set forth below, many of the devices and methods disclosed in the patents of Table 1 and elsewhere herein may be modified advantageously by using the teachings of the present invention. However, the listing of any such patents in Table 1 is by no means an indication that such patents are prior art to the present invention.

SUMMARY OF THE INVENTION

The present invention has certain objects. That is, various embodiments of the present invention provide solutions to one or more problems existing in the prior art with respect to protection from electrical interference in medical devices, particularly in implantable medical devices. One of such problems involves the complexity of feedthrough assemblies for implantable medical devices which maintain adequate protection from external electrical interference. Further, other problems include: excessive congestion in implantable medical devices; requirement for a large number of discrete components to provide adequate protection from external electrical interference; undesirable effects of long wire lengths in feedthrough assemblies; relative complexity of assembling implantable medical devices using conventional protection against external electrical interference; high cost associated with complex feedthrough assemblies; and lack of the ability to integrate protection into an automated manufacturing process.

In comparison to known techniques for providing protection against electrical interference for circuitry of implantable medical devices, various embodiments of the present invention may provide one or more of the following advantages. For example, improved device performance may occur due to adequate protection from electrical interference such as voltage and current surges and from a decrease in wire length. Further, for example, the cost of assembling implantable medical devices may be reduced due to the use of common feedthrough techniques as opposed to complex feedthrough assemblies. In addition, the ability to integrate such protection into the medical device using automated processing may be achieved. Yet, further, the present invention provides a feedthrough which effectively protects against external electrical interference.

Some embodiments of the present invention include one or more of the following features: a feedthrough assembly including at least one electrically conductive pin extending through an aperture in the case of an implantable medical device; a zener diode assembly including a diode protection circuit mounted on a printed circuit board; a printed circuit board used for formation of at least a part of an electrical conductive path for connection of at least one electrically conductive pin of a feedthrough to a medical device circuit assembly mounted within the case of an implantable medical device (e.g., the medical device circuit assembly being a circuit assembly that is separate and remote from the protection circuit board); a printed circuit board having a diode protection circuit mounted thereon which provides for electrical connection of the diode protection circuit between an electrically conductive pin of a feedthrough and the case of an implantable medical device; a printed circuit board that includes a first side having at least one conductive pin region for electrical connection to an electrically conductive pin of a feedthrough and a second side opposite the first side upon which a diode protection circuit is mounted; and a printed circuit board that includes conductive traces for use in electrically connecting a diode protection circuit mounted thereon between at least one pin conductive region of the printed circuit board and a case conductive region which is connected to the case of an implantable medical device.

Further, other features may include: a flip chip diode array component that is used for circuit protection purposes; wire bonding of a printed circuit board having diode protection circuitry mounted thereon to a circuit assembly in the implantable medical device including circuitry for performing the applicable functions of such device; positioning of a printed circuit board such that electrically conductive pins of feedthroughs for an implantable medical device are directly connected to conductive pin regions of the printed circuit board and further wherein such conductive pin regions of the printed circuit board may be aligned to corresponding electrically conductive pins of the feedthroughs; an implantable medical device including one or more electrically conductive pin(s) of feedthrough(s) with each conductive pin having applicable zener diode protection connected between the respective pin and the case of the implantable medical device; a printed circuit board, distinct from the circuit assembly including circuitry for the particular implantable medical device, having a diode array component mounted thereon for providing protection of multiple feedthroughs; and methods of providing a feedthrough assembly for an implantable medical device using a printed circuit board including one or more features described above, e.g., a diode array mounted thereon, direct electrical connection of a feedthrough pin to pin conductive regions of the printed circuit board, alignment of the feedthrough pins to pin conductive regions of the printed circuit board, etc.

BRIEF DESCRIPTION OF THE DRAWINGS

FIG. 2 is a bottom view of an implantable medical device including electrical interference protection according to the present invention and generally showing a feedthrough region of an implantable medical device.

FIG. 3 is a diagram of an illustrative feedthrough useable in the feedthrough assembly of the present invention.

FIG. 4 is a general block schematic diagram of electrical interference protection circuitry connected to medical device circuitry according to the present invention.

FIG. 5 is a cut-away top view of a portion of the feedthrough region of the medical device shown in FIG. 2 with a portion of the metal case of the implantable medical device removed showing a printed circuit board and diode array mounted thereon electrically connected to the medical device circuitry according to the present invention.

FIG. 6 is a cut-away top view of the implantable medical device shown in FIG. 5 with the protection circuitry shown in FIG. 5 removed illustrating the numerous feedthroughs of the implantable medical device under the protection circuitry.

FIGS. 7A–7C are bottom view, top view, and side view, respectively, of an illustrative printed circuit board according to the present invention.

Detailed Description of the Embodiments

Figure 1:
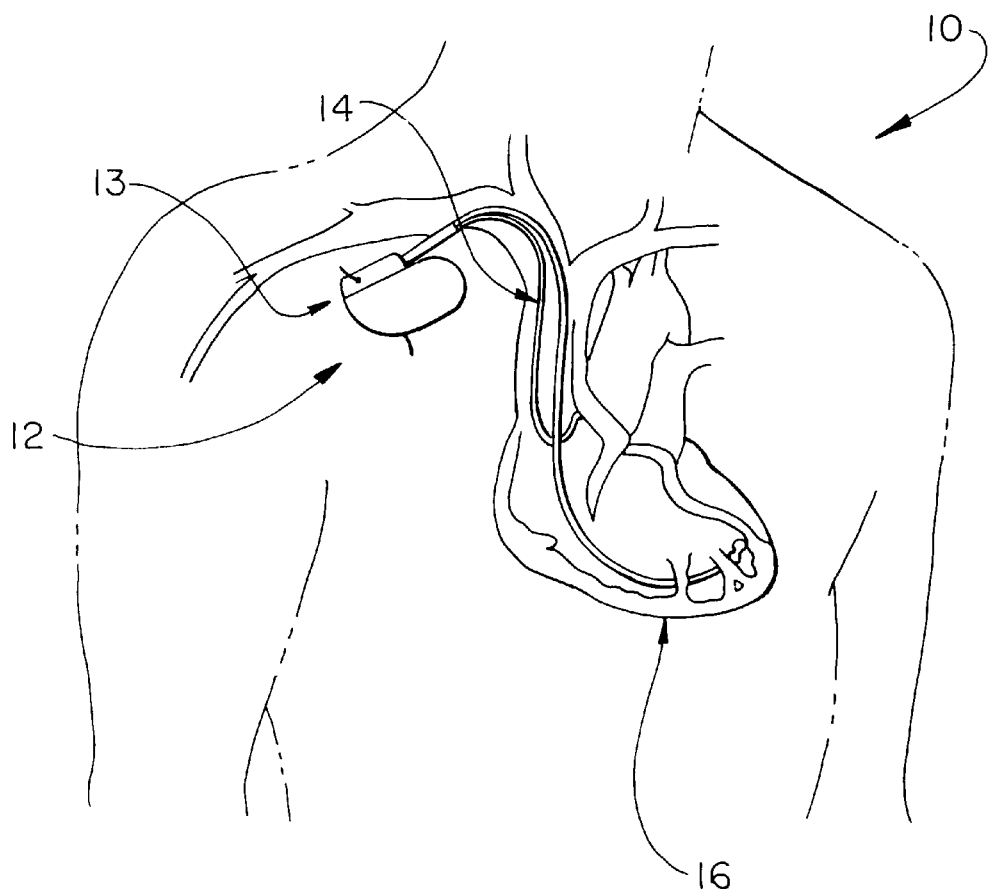
FIG. 1 is a diagram illustrating an implantable medical device in a body; the medical device including electrical interference protection according to the present invention.

The present invention relates to feedthrough assemblies and methods of providing such feedthrough assemblies for medical devices, particularly implantable medical devices. FIG. 1 is a schematic view of an implantable medical device 12 embodying the present invention, wherein the implantable medical device 12 includes protection against electrical interference according to the present invention. At least one lead 14 is connected to the implantable medical device 12 in connector block region 13 using feedthrough(s). The implantable medical device 12 may be implanted near a human heart 16.

In the case where implantable medical device 12 is a pacemaker implanted in a body 10, the pacemaker 12 includes at least one or both of pacing and sensing leads represented generally as leads 14 to sense electrical signals attendant to the depolarization and repolarization of the heart 16, and to provide pacing pulses for causing depolarization of cardiac tissue in the vicinity of the distal ends thereof. For example, implantable medical device 12 may be an implantable cardiac pacemaker such as that described in U.S. Pat. No. 5,158,078 to Bennett et al.; U.S. Pat. No. 5,312,453 to Shelton et al.; or U.S. Pat. No. 5,144,949 to Olson et al., hereby incorporated herein by reference in their respective entireties.

Implantable medical device 12 may also be a pacemaker-cardioverter-defibrillator (PCD) corresponding to any of the various commercially-available implantable PCDs. The present invention may be practiced in conjunction with PCDs such as those described in U.S. Pat. No. 5,545,186 to Olson et al.; U.S. Pat. No. 5,354,316 to Keimel; U.S. Pat. No. 5,314,430 to Bardy; U.S. Pat. No. 5,131,388 to Pless; or U.S. Pat. No. 4,821,723 to Baker, et al., all hereby incorporated herein by reference in their respective entireties.

Alternatively, implantable medical device 12 may be an implantable neurostimulator or muscle stimulator such as that disclosed in U.S. Pat. No. 5,199,428 to Obel et al.; U.S. Pat. No. 5,207,218 to Carpentier et al.; or U.S. Pat. No. 5,330,507 to Schwartz, or an implantable monitoring device such as that disclosed in U.S. Pat. No. 5,331,966 to Bennett et al., all of which are hereby incorporated by reference herein in their respective entireties.

Further, for example, the implanted device 12 may be a defibrillator, an implantable cardioverter/defibrillator (ICD), a brain stimulator, a gastric stimulator, a drug pump, or any other implantable device that would benefit from the protection described herein. Therefore, the present invention is believed to find wide application in any form of implantable electrical device. For example, although the present invention is described in conjunction with an illustrative dual chamber pacemaker having four feedthroughs, the present invention is applicable to any other pacemaker having one or more feedthroughs and to other implantable medical devices having one or more feedthroughs wherein protection from electrical interference is desired.

FIG. 2 shows a bottom view of an illustrative implantable medical device 12, e.g., a dual chamber pacemaker. The implantable medical device 12 includes a metal case 20 made of any suitable conductive material, such as titanium or a titanium alloy. The implantable medical device 12 further includes a connector block 22 including two receptacles 31 and 32 for receiving leads 14, i.e., first lead 17 and second lead 19.

Further, feedthrough region 21 is shown including four feedthroughs 24–27.

Generally, the implantable medical device 12 may have multiple leads 14, each including one or more conductors, such as for sensing physiological parameters, for use as stimulation electrodes, etc. Pacemakers are most commonly operated in conjunction with one or more leads, for conveying cardiac stimulating pulses from the pacemaker to the patient's heart, and for conveying electrical cardiac signals from the heart to the pacemaker's sensing circuitry. At least two different types of pacemaker leads, unipolar and bipolar, are commonly known and used.

Unipolar leads have only a single electrode and a single electrical conductor therein. The electrode is disposed at or near the distal end of the lead, which is situated in some particular location in the patient's heart. For example, the distal end may be situated at the apex of the heart in the right ventricle, in the atrial chamber, or in the coronary sinus. The single electrode and conductor of a unipolar lead in conjunction with the pacemaker case (e.g., as the indifferent electrode) is used both for sensing (that is, for conducting electrical cardiac signals from the heart to the pacemaker) and for pacing (that is, for delivering stimulating pulses from the pacemaker to the heart).

Bipolar leads have two electrodes and two electrically isolated conductors therein. Often, one electrode, called the "tip" electrode, is a conductive contact disposed at the distal end of the lead, while a second electrode, called the "ring" electrode, is a conductive ring disposed on the lead body some distance back from the distal end of the lead. The two isolated conductors conduct signals (pace and sense) between the pacemaker and the cardiac tissue in close proximity to the electrodes.

For simplicity, although various lead configurations are possible, the remaining portion of the description herein shall be limited to the use of two 2-wire leads, i.e., first lead 17 and second lead 19. The first lead 17 is inserted in receptacle 31 and the second lead 19 is inserted in receptacle 32. The conductors of the respective leads inserted in receptacles 31 and 32 are connected to medical device circuitry 50 within case 20 using the array of feedthroughs 24–27 as shown in FIG. 2 and elsewhere herein.

In the illustrative implantable medical device 12 described herein, feedthrough 24 is for connecting a first conductor of the first lead 17 inserted in receptacle 31 into the interior of case 20 and feedthrough 25 is used for connecting a second conductor of the first lead 17 received in receptacle 31 into the interior of case 20. Likewise, feedthrough 26 is used for connecting a first conductor of the second lead 19 inserted in receptacle 32 into the interior of case 20 and feedthrough 27 is used for connecting a second conductor of the second lead 19 into the interior of case 20. With respect to the dual chamber pacemaker illustrative embodiment described herein, feedthrough 26 connects a tip electrode to a ventricle of heart 16 ($V_{TIP}$) into the interior of case 20 and feedthrough 27 connects a ring electrode from 10 the ventricle of the heart ($V_{RING}$) into the interior of case 20. Likewise, feedthrough 24 connects an atrial tip electrode from the heart ($A_{TIP}$) into the interior of the case 20 and feedthrough 25 connects a ring electrode extending to the atrium of the heart ($A_{RING}$) into the interior of case 20. However, one skilled in the art will recognize from the description herein, that the feedthrough assembly according to the present invention may be used to connect any desired number and type of conductors from the exterior of the case 20 to the interior thereof, independent of the use for such conductors, e.g., sensing, pacing, etc.

The connector block 22 is generally formed of a biocompatible material such as silicon including receptacles defined therein and disposed about pin portions 34–37. The connector block 22 is connected to the case 20 at feedthrough region 21 which includes the array of feedthroughs 24–27.

FIG. 3 is one illustrative feedthrough which may be used in conjunction with the illustrative implantable medical device 12 described herein. It will be recognized that with use of the protection circuitry described herein, particularly in combination with the manner of providing a feedthrough assembly having such protection circuitry as described herein, various feedthrough configurations may be used in the feedthrough assembly according to the present invention. For example, FIG. 3 shows feedthrough 24 which is a generally conventional feedthrough including a ferrule 76 disposed around an electrically conductive pin 34 supported by an insulator 78; the pin 34 having a longitudinal axis 75 extending therethrough. The insulator 78 is secured to the ferrule 76 by means of a braised joint 84. Similarly, the electrically conductive pin 34 is secured to the insulator 78 by way of a braised joint 82. Case 20 includes an exterior surface 21 and an interior surface 22. The feedthrough 24 in FIG. 3 is shown in sealing engagement with one side, i.e., exterior surface 21, of case 20. With the feedthrough 24 in sealing engagement with case 20, a first end 74 of electrically conductive pin 34 projects from interior surface 22 of case 20 into the interior of case 20 and may be terminated with a pin termination pad 79, e.g., a Kovar pad. The pin termination pad 79 generally lies perpendicular to the longitudinal axis 75 extending through the pin 34. A second end 72 of electrically conductive pin 34 projects from the exterior surface 21 to the exterior of the case 20. Generally, the ferrule 76 is sealed to the case 20 by welding.

As shown in FIG. 2, each of the exterior ends, e.g., second end 72 of electrically conductive pin 34, extends for connection to a corresponding conductor of a lead, e.g., first lead 17, inserted into receptacles 31 and 32 of connector block 22. The interior ends, e.g., second end 74 of electrically conductive pin 34, projects into the interior of metal case 20 in feedthrough region 21 for connection to medical device circuitry 50 (FIG. 5) also located within the interior of metal case 20.

FIG. 4 is a schematic block diagram showing the electrical connection of the conductors of the leads 17, 19 provided to the interior of case 20 using the electrically conductive pins 34–37 of the array of feedthroughs 24–27 to medical device circuitry 50 mounted within case 20. The inputs provided to the interior of case 20 by way of the array of feedthroughs 24–27 are connected to protection circuitry 52 which is employed to provide protection from electrical interference, e.g., protection of medical device circuitry 50 from current and voltage surges such as defibrillation pulses or other externally generated interference.

Medical device circuitry 50 as shown in FIG. 4 may include any circuitry required for performing the desired functionality of the implantable medical device 12. For example, as implantable medical device 12 may be a pacemaker, a PCD, a defibrillator, or any other medical device, medical device circuitry 50 may encompass circuitry for providing the functionality of such devices. Again, for simplicity and illustrative purposes, medical device circuitry 50 is circuitry for providing the functionality of a dual chamber pacemaker with the medical device circuitry 50 being provided with inputs $V_{TIP}$, $V_{RING}$, $A_{TIP}$, and $A_{RING}$ through the feedthrough assembly according to the present invention.

Likewise, generally, protection circuitry 52 may include any suitable protection circuitry for protecting medical device circuitry 50 from external electrical interference, e.g., voltage and current surges at inputs provided by feedthroughs into the interior of case 20. In one particular illustrative embodiment of protection circuitry 52 wherein the inputs include $V_{TIP}$, $V_{RING}$, $A_{TIP}$, and $A_{RING}$, the protection circuitry 52 includes connection of back-to-back zener diodes between the input and the metal case. For example, the protection circuitry 52 as shown in FIG. 4 includes a zener diode 56 and a zener diode 65 connected in back-to-back configuration between the $V_{TIP}$ input and case 20. Likewise, zener diodes 57 and 65 provide a back-to-back configuration between input $V_{RING}$ and case 20, zener diodes 59 and 65 provide a back-to-back configuration between input $A_{RING}$ and case 20, and zener diodes 58 and 65 provide a back-to-back configuration between input $A_{TIP}$ and case 20. In this configuration, the diodes form a conventional back-to-back arrangement which breaks down at a predetermined voltage to provide protection against excessive voltage and/or current surges at the inputs provided via the feedthroughs 24–27.

FIG. 5 is a cutaway top view of a portion of the implantable medical device 12 shown in FIG. 2 including the feedthrough region 21 which shows the incorporation of protection circuitry 52 into the implantable medical device 12 by way of feedthrough assembly 118. The case 20 of the implantable medical device 12 is partially removed. The feedthrough assembly 118 includes a protection circuit assembly 120 including a printed circuit board 121 having the protection circuitry 52, e.g., a diode array, mounted thereon. The feedthrough assembly 118 further includes feedthroughs 24–27. However, such feedthroughs 24–27 are not shown in FIG. 5 as the feedthroughs 24–27 lie directly below the printed circuit board 121 of the protection circuit assembly 120. FIG. 5 further shows the medical device circuitry 50 which is an assembly generally including components 98 mounted on a substrate, e.g., a printed circuit board 51, a ceramic substrate, etc., for performing one or more various functions of the medical device 12.

The printed circuit board 121 of protection circuit assembly 120 provides for electrical conductive paths for electrical connection of each of the electrically conductive pins 34–37 to the medical device circuitry 50. Further, printed circuit board 121 provides for electrical connection of protection circuitry 52, e.g., a diode protection circuit, to the respective inputs provided by electrically conductive pins 34–37. The printed circuit board 121 is distinct from printed circuit board 51, or alternatively ceramic substrate, of medical device circuitry 50.

As used herein, a printed circuit board being distinct from another printed circuit board or ceramic substrate refers to the two elements being separate from one another wherein an electrical connection between electrically conductive regions of each element is necessary for the transmission of signals therebetween, e.g., a wire bond electrical connection. Although it is preferable that the printed circuit board 121 be distinct from printed circuit board 51, it is possible to provide a single printed circuit board for providing the functions of both printed circuit board 121 and printed circuit board 51. Using a distinct printed circuit board 121 provides electrical interference protection at the feedthrough site away from the circuitry 50. In other words, the distinct printed circuit board 121 reduces potential coupling between electrical interference on printed circuit board 121 and the sensitive circuits on printed circuit board 51, e.g., reradiation or crosstalk is reduced due to the separation. Further, a distinct board allows the same protection technique to be used for multiple medical device designs. In addition, the board is inexpensive, can be optimized for high power (i.e., voltage and current), and can be optimized in size (e.g., placed over feedthroughs for literally a direct connection).

FIG. 6 is a top view of the portion of implantable medical device 12 as shown in FIG. 5 with the case 20 partially removed and also without the protection circuit assembly 120. As such, printed circuit board 121 of feedthrough assembly 118 is removed and not connected to respective pads 90–94 of medical device circuitry 50 mounted in case 20. Each of the feedthroughs 24–27 shown in FIG. 6 include a portion of the ferrule 76 in sealing engagement with the case 20 and a pin termination pad 79 of pin 34 supported by insulator 78 as shown with reference to ferrule 24.

One skilled in the art will recognize that the feedthroughs 24–27 may be of any number of different configurations. For example, another configuration of a feedthrough is shown in U.S. Pat. No. 5,735,884 to Thompson, et al., which allows for the connection of capacitors on the feedthrough to protect it from electromagnetic interference (EMI). The present invention is not limited to any particular configuration of feedthrough, as long as the feedthroughs provide one or more electrically conductive pins insulated from case 20 for provision of signals from the exterior of the case 20 to the interior thereof.

Figure 7C:
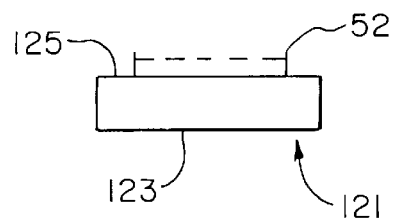

FIGS. 7A–7C show the printed circuit board 121 in more detail. A bottom view of the printed circuit board 121 is shown in FIG. 7A, a top view in FIG. 7B, and a side view in FIG. 7C. As shown in the bottom view of the printed circuit board 121 of FIG. 7A, the printed circuit board 121 includes four circular conductive pin contact regions 150–153 on a first side 123 of the board 121. Such regions 150–153 are for direct contact, i.e., no other elements necessary for the electrical connection, to the pin termination pads 79 of pins 34–37 shown in FIG. 6. In other words, the termination pads 79 are connected in direct contact with the circular conductive pin contact regions 150–153. Such connection may be accomplished using brazing, conductive epoxy, soldering, welding, etc. One skilled in the art will recognize from the description herein that the pins 34–37 may be connected directly to the regions 150–153 without the use of the termination pads 79.

Preferably, the conductive pin contact regions 150–153 are aligned such that the pin length (L) (shown in FIG. 3) of the electrically connected pins 34–37 extending to the interior of the case 20 is kept to the shortest length (L) possible. For example, the conductive pin contact regions 150–153 of the printed circuit board may be directly positioned such that a longitudinal axis 75 through the pin is generally perpendicular to a plane defined by the printed circuit board 121, and further may be perpendicular to a plane defined by a side of the case 20 parallel to the plane defined by the printed circuit board 121. At a minimum, the printed circuit board 121 is mounted so that the conductive pin contact regions 150–153 are in a region adjacent feedthroughs 24–27. With such an arrangement, losses occurring due to pin lengths and inductive effects thereof are reduced.

Rectangular conductive case contact region 155 is for connection to metal case 20. For example, this connection may be made by using a terminal block 41 that is attached between the center feedthroughs 25, 26 as shown in FIG. 6. The terminal block 41 may be attached to the case 20 by, for example, spot welding, resistance welding, or brazing. The block 41 may also be an integral part of the case 20. The conductive case contact region 155 may be connected to the terminal block 41 by brazing, conductive epoxy, soldering, welding or any other connection method. Regions surrounding the contact regions 150–153 are insulative portions of the printed circuit board 121.

FIG. 7B shows a second side 125 of printed circuit board 121 opposite the first side 123 whereon the protection circuitry 52, e.g., a zener diode array, is mounted. As shown in FIG. 7B, the second side 125 of the printed circuit board 121 includes conductive die contact regions 180–183 for connection to die bond pad regions of the diode protection circuitry 52; the protection circuitry 52 is shown in dashed lines in FIG. 7C. The conductive die contact regions 180–183 are electrically connected to medical device contact regions 140–143 by conductive traces 206–209, respectively. The elongated die case contact region 185 is for connection to a case die bond pad region of the diode protection circuitry 52 for electrical connection of the circuit to case 20. The elongated die case contact region 185 is connected to case contact region 155 on the bottom side 123 of the printed circuit board 121 and also to another case contact region 145 on the top side 125 of the printed circuit board 121. Such connection is facilitated by case contact via 165. Conductive vias 161–164 are respectively used in conjunction with signal conductive layers in the printed circuit board 121 for connection of conductive pin contact regions 150–153 to the electrical conductive path established between the respective conductive die contact regions 180–183 and the conductive medical device contact regions 140–143. Once again, various insulative regions of the printed circuit board 121 are shown surrounding the conductive regions.

Various conductive and insulative materials of the printed circuit board 121 may be used. For example, the board may be a ceramic or epoxy board, a co-fired ceramic board, or the board material may include FR5 or a similar material with high $T_G$, i.e., glass transition temperatures, such as for use in flip chip processes. The printed circuit board 121 may be a two-layer design, or can be any multi-layer design. For example, the printed circuit board 121 may be a four-layer design. In other words, the printed circuit board 121 may include two conductive signal layers isolated from and sandwiched between top and bottom conductive printed layers. The top and bottom layers are connected to the case contact wherever possible, and signal layers are in the center to reduce radiated noise. Minimum spacing between the traces of the printed circuit board is preferably about 5 mils with a minimum 5 mil conductive trace. Preferably, current carrying traces are as wide as possible to reduce resistance. The copper thickness of the traces is approximately 1 oz/square foot (i.e., 1 oz). Thinner copper may be used (e.g., 0.5 oz), but will result in an increase in the resistance of the traces. Also, thicker copper may be used (e.g., 2 oz), but such thickness is limited by the smallest width of the traces or aspect ratio of the traces. Further, plating is preferably immersion gold over electrolyzed nickel, or any other suitable plating for aluminum wire bonding.

The board thickness may vary, however, the thickness is preferably kept to a minimum. For example, a 62 mil board may be used. Likewise, the dimensional characteristics of the board are kept to a minimum; for example, such as about 510 mils by 145 mils. Although various characteristics of the board are listed above, others may be equally suitable. For example, any dimensional configuration having the desired characteristics for the particular application may be used. Therefore, generally, as used herein, printed circuit board refers to any substrate or material including conductive traces for providing desired electrical connections, e.g., connections for a diode array component to contact regions at a surface of the board.

The conductive medical device contact regions 140–143 are connected to conductive pads 90–93 of printed circuit board 51 of medical device circuitry 50 as shown in FIG. 5. The connections between the printed circuit board 121 and the medical device circuit board 51 are preferably performed by wire bonding using wires 101–104, respectively. Note, however, that connections between board 121 and board 51 may also be established using flex circuit or any other suitable interconnection method. Further, case contact region 145 is connected to medical device circuitry pad 94 by wire bonding using wire 105. For example, such wires, e.g., 5 mil aluminum wires, may be wire bonded using an ultrasonic wedge bonder.

The protection circuitry 52 of the feedthrough assembly 118 is mounted over die contact regions 180–183 of circuit board 121. Although various zener diode configurations may be used, preferably, the protection for each input corresponding to each feedthrough 24–27 in feedthrough region 21 is provided by a back-to-back zener diode configuration shown in FIG. 4 and also in FIG. 8. In other words, each input is provided with a two zener diode back-to-back configuration between the input and case 20.

Figure 8:
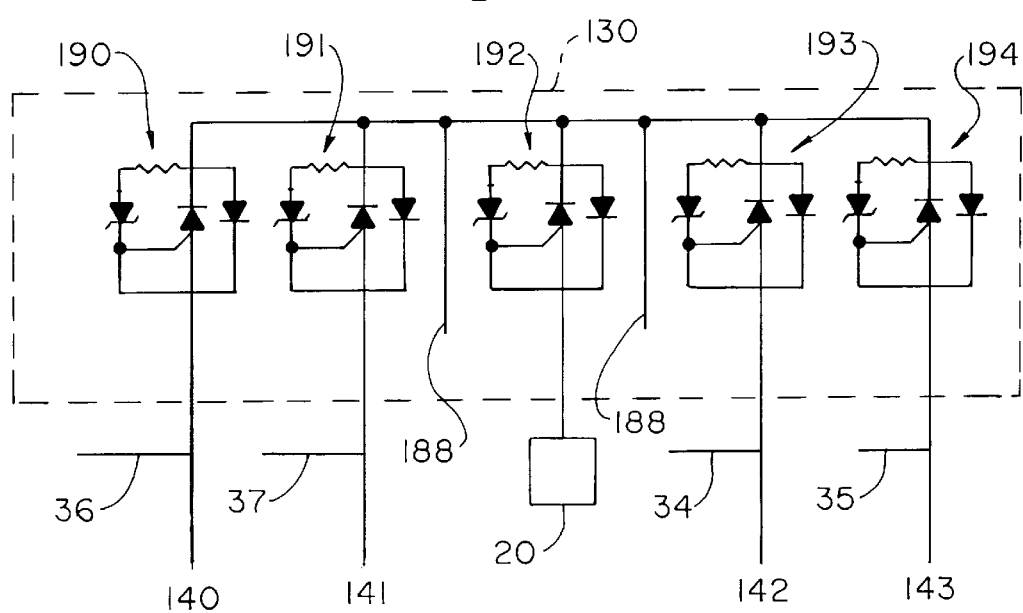
FIG. 8 is a detailed schematic diagram of protection circuitry provided by a particular diode array component according to the present invention.

Preferably, in accordance with the present invention, the protection circuitry 52 is provided using a diode array component 130 such as that shown in the schematic of FIG. 8. Preferably, the part is a flip chip component so as to eliminate space required for additional connection of the diode component to the printed circuit board 121, such as wire bonding component die bond pads to the printed circuit board 121.

Preferably, the diode array consists of five zener diode triggered semiconductor controlled rectifiers (SCR's) with anti-parallel diodes arranged in an array with one common connection. This preferred configuration is shown in FIG. 8 with the five zener diode triggered SCR's 190–194. This allows for a small footprint despite the large currents that may be carried through the device during defibrillation, e.g., 10 amps. The SCR's 190–194 turn on and limit the voltage across the device when excessive voltage and current surges occur.

As shown in the schematic of FIG. 8, each of the zener diode triggered SCR's 190–194 is connected to an electrically conductive pin 34–37, respectively. Further, each electrically conductive pin 34–37 is connected to a medical device contact region 140–143 to be wire bonded to pads 90–93 of printed circuit board 51. The diode array component 130 is connected to the electrically conductive pins 34–37 via the die contact regions 180–184, respectively, along with other electrical conductive traces of the printed circuit board 121. Further, as shown in FIGS. 5, 7B and 8, substrate contacts 188 are provided for additional connections to the circuitry 50 to be protected where the output circuit design requires such connection. Further, they also allow for each diode in the diode array to be tested individually. For example, in FIGS. 5 and 7B, substrate contacts 188 are connected to a substrate contact pad 147 by conductive trace 211. The substrate contact pad 147 may then be wire bonded to a conductive pad region 107 on printed circuit board 51.

In the schematic as shown in FIG. 8, a back-to-back configuration of zener diodes is provided for the input of electrically conductive pin 34 by zener diode triggered SCR's 193 and 192. Likewise, the back-to-back configuration of SCR's 194 and 192 is provided for the input of electrically conductive pin 35, the back-to-back configuration for the input provided by electrically conductive pin 36 is provided by SCR's 190 and 192, and, lastly, protection for input 37 is provided by zener diode triggered SCR's 191 and 192. Each of the back-to-back configurations is connected between the input and case 20.

By providing a feedthrough assembly 118 according to the present invention as shown in the figures, assembly of the implantable medical device 12 is simplified. For example, discrete zener diode components are not required in view of the use of a diode array component 130 mounted on printed circuit board 121. The mounting of board 121 within the implantable medical device is easily performed as the procedures required are generally procedures typically used in automated assembly of the device, e.g., such as those used for preparing and mounting printed circuit board 51 within the implantable medical device 12. Further, with use of the printed circuit board 121 to provide connection of the inputs to the medical device circuitry 50 by way of printed circuit board 121 mounted relative to printed circuit board 51, stray signals, e.g., noise, is reduced due to insulative characteristics of board 121 used to transmit the inputs.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to the use of the particular zener diode array components listed herein, but such protection circuitry may be provided by other zener diode configurations. Further, the feedthroughs described herein are given for illustrative purposes only and such feedthroughs used for the medical device may encompass any suitable or desirable type of feedthrough. The present invention is also not limited to use in connection with pacemakers but may also be used with any other type of medical device, such as defibrillators, stimulators, etc. In addition, the present invention further includes within its scope other methods of making and using the invention described herein above.

What is claimed is:

1. A feedthrough assembly of an implantable medical device, the implantable medical device having a case with an interior and exterior surface, wherein the implantable medical device includes a medical device circuit assembly mounted within the case, the feedthrough assembly comprising:
   at least one electrically conductive pin extending through an aperture in the case such that the electrically conductive pin includes a first end projecting from the exterior surface of the case and a second end projecting from the interior surface of the case, the electrically conductive pin being insulated from the case; and
   a protection circuit assembly including:
      a diode protection circuit, and
      a printed circuit board having the diode protection circuit mounted thereon, wherein the printed circuit board forms at least a part of an electrical conductive path for connection of the at least one electrically conductive pin to the medical device circuit assembly mounted within the case, and further wherein the printed circuit board provides for electrical connection of the diode protection circuit mounted thereon between the at least one electrically conductive pin and the case.

2. The feedthrough assembly of claim 1, wherein the printed circuit board includes a first side having at least one conductive pin contact region for electrical connection to the at least one electrically conductive pin, wherein the printed circuit board includes a second side opposite the first side upon which the diode protection circuit is mounted, wherein the printed circuit board includes at least one conductive case contact region for electrical connection to the case, wherein the printed circuit board includes at least one conductive medical device contact region for electrical connection to the medical device circuit assembly mounted within the case, and further wherein the printed circuit board includes conductive traces for use in electrically connecting the diode protection circuit between the at least one conductive pin contact region and the at least one conductive case contact region.

3. The feedthrough assembly of claim 1, wherein the diode protection circuit includes at least a first zener diode and a second zener diode in a back to back configuration.

4. The feedthrough assembly of claim 1,
   wherein the at least one electrically conductive pin includes two or more electrically conductive pins with each electrically conductive pin extending through an aperture in the case such that the electrically conductive pin includes a first end projecting from the exterior surface of the case and a second end projecting from the interior surface of the case, and further wherein each electrically conductive pin is insulated from the case, and
   further wherein the diode protection circuit includes at least a first zener diode, a second zener diode and a third zener diode, wherein the first zener diode is connected to one of the two or more electrically conductive pins using the printed circuit board, wherein the second zener diode is connected to another of the two or more electrically conductive pins using the printed circuit board, wherein each of the first and second zener diodes is connected to the third zener diode, and further wherein the third zener diode is connected to the case such that the first and third zener diodes are in a back to back configuration between the one of the two or more electrically conductive pins and the case and such that the second and third zener diodes are in a back to back configuration between another of the two or more electrically conductive pins and the case.

5. The feedthrough assembly of claim 1, wherein the diode protection circuit is a flip chip diode array component mounted on the printed circuit board.

6. The feedthrough assembly of claim 2, wherein the medical device contact regions of the printed circuit board are wire bonded to corresponding pads of the medical device circuit assembly.

7. The feedthrough assembly of claim 2, wherein the at least one electrically conductive pin is directly connected to the at least one conductive pin contact region of the printed circuit board.

8. The feedthrough assembly of claim 7, wherein the at least one electrically conductive pin is aligned with the at least one conductive pin contact region of the printed circuit board.

9. A feedthrough assembly of an implantable medical device, the implantable medical device having a case with an interior and exterior surface, wherein the implantable medical device includes a medical device circuit assembly mounted within the case, the feedthrough assembly comprising:

two or more electrically conductive pins, wherein each electrically conductive pin extends through an aperture in the case such that the electrically conductive pin includes a first end projecting from the exterior surface of the case and a second end projecting from the interior surface of the case, and further wherein each electrically conductive pin is insulated from the case;

a diode array component including at least a first zener diode, a second zener diode and a third zener diode; and a printed circuit board, distinct from the medical device circuit assembly, having the diode array component mounted thereon, wherein the printed circuit board forms at least a part of the electrical conductive paths for connection of each of the two or more electrically conductive pins to the medical device circuit assembly mounted within the case, and further wherein the first and third zener diodes are in a back to back configuration and connected between one of the two or more electrically conductive pins and the case using the printed circuit board and the second and third zener diodes are in a back to back configuration and connected between another of the two or more electrically conductive pins and the case using the is printed circuit board.

10. The feedthrough assembly of claim 9, wherein the first zener diode is connected to one of the two or more electrically conductive pins using the printed circuit board, wherein the second zener diode is connected to another of the two or more electrically conductive pins using the printed circuit board, wherein each of the first and second zener diodes is connected to the third zener diode, and further wherein the third zener diode is connected to the case such that the first and third zener diodes are in the back to back configuration between one of the two or more electrically conductive pins and the case and the second and third zener diodes are in a back to back configuration between another of the two or more electrically conductive pins and the case.

11. The feedthrough assembly of claim 9, wherein the printed circuit board includes a first side having two or more conductive pin contact regions with each conductive pin contact region for electrical connection to one of the two or more electrically conductive pins, wherein the printed circuit board includes a second side opposite the first side upon which the diode array component is mounted, wherein the printed circuit board includes at least one conductive case contact region for electrical connection to the case, wherein the printed circuit board includes at least one conductive medical device contact region for electrical connection to the medical device circuit assembly mounted within the case, and further wherein the printed circuit board includes conductive traces for use in electrically connecting the diode array component between the two or more conductive pin contact regions and the at least one conductive case contact region.

12. The feedthrough assembly of claim 9, wherein the diode array component is a flip chip diode array component mounted on the printed circuit board.

13. The feedthrough assembly of claim 11, wherein the medical device contact regions of the printed circuit board are wire bonded to corresponding pads of the medical device circuit assembly.

14. The feedthrough assembly of claim 11, wherein each of the two or more electrically conductive pins is directly connected to a conductive pin contact region of the printed circuit board.

15. The feedthrough assembly of claim 14, wherein each of the two or more electrically conductive pins has a longitudinal axis therethrough that is perpendicular to a plane defined by a side of the printed circuit board.

16. A method of providing a feedthrough assembly for an implantable medical device, the implantable medical device having a case with an interior and exterior surface, wherein the implantable medical device includes a medical device circuit assembly mounted within the case, the method comprising:

positioning at least one electrically conductive pin through an aperture in the case such that the electrically conductive pin includes a first end projecting from the exterior surface of the case and a second end projecting from the interior surface of the case, the electrically conductive pin being insulated from the case;

providing a protection circuit assembly including a diode protection circuit mounted on a printed circuit board; and electrically connecting the at least one electrically conductive pin to at least one conductive pin contact region of the printed circuit board;

electrically connecting conductive medical device contact regions of the printed circuit board to corresponding conductive regions of medical device circuit assembly; and electrically connecting at least one conductive case contact region of the printed circuit board to the case, wherein the printed circuit board includes conductive traces for electrically connecting the diode protection circuit mounted thereon between the at least one conductive pin contact region and the at least one conductive case contact region.

17. The method of claim 16, wherein the printed circuit board includes a first side including the at least one conductive pin contact region for electrical connection to the at least one electrically conductive pin, and further wherein the printed circuit board includes a second side opposite the first side upon which the diode protection circuit is mounted.

18. The method of claim 17, wherein the diode protection circuit includes at least a first zener diode and a second zener diode in a back to back configuration.

19. The method of claim 16, wherein electrically connecting conductive medical device contact regions of the printed circuit board to corresponding conductive regions of medical device circuit assembly includes wire bonding the conductive medical device contact regions of the printed circuit board to the corresponding conduct regions of the medical device circuit assembly.

20. The method of claim 16, wherein electrically connecting the at least one electrically conductive pin to the at least one conductive pin contact region of the printed circuit board includes directly connecting the at least one electrically conductive pin to the conductive pin contact region of the printed circuit board.

21. An implantable medical device comprising:
a case having an interior and exterior surface;
a medical device circuit assembly mounted within the case;
at least one electrically conductive pin extending through an aperture in the case such that the electrically conductive pin includes a first end projecting from the exterior surface of the case and a second end projecting from the interior surface of the case, the electrically conductive pin being insulated from the case; and
a protection circuit assembly including:
a diode protection circuit, and
a printed circuit board having the diode protection circuit mounted thereon, wherein the printed circuit board forms at least a part of an electrical conductive path for connection of the at least one electrically conductive pin to the medical device circuit assembly mounted within the case, and further wherein the printed circuit board provides for electrical connection of the diode protection circuit mounted thereon between the at least one electrically conductive pin and the case.

22. The device of claim 21, wherein the printed circuit board includes a first side having at least one conductive pin contact region for electrical connection to the at least one electrically conductive pin, wherein the printed circuit board includes a second side opposite the first side upon which the diode protection circuit is mounted, wherein the printed circuit board includes at least one conductive case contact region for electrical connection to the case, wherein the printed circuit board includes at least one conductive medical device contact region for electrical connection to the medical device circuit assembly mounted within the case, and further wherein the printed circuit board includes conductive traces for use in electrically connecting the diode protection circuit between the at least one conductive pin contact region and the at least one conductive case contact region.

23. The device of claim 21, wherein the diode protection circuit includes at least a first zener diode and a second zener diode in a back to back configuration.

24. The device of claim 21,
wherein the at least one electrically conductive pin includes two or more electrically conductive pins with each electrically conductive pin extending through an aperture in the case such that the electrically conductive pin includes a first end projecting from the exterior surface of the case and a second end projecting from the interior surface of the case, and further wherein each electrically conductive pin is insulated from the case, and
further wherein the diode protection circuit includes at least a first zener diode, a second zener diode and a third zener diode, wherein the first zener diode is connected to one of the two or more electrically conductive pins using the printed circuit board, wherein the second zener diode is connected to another of the two or more electrically conductive pins using the printed circuit board, wherein each of the first and second zener diodes is connected to the third zener diode, and further wherein the third zener diode is connected to the case such that the first and third zener diodes are in a back to back configuration between the one of the two or more electrically conductive pins and the case and such that the second and third zener diodes are in a back to back configuration between another of the two or more electrically conductive pins and the case.

25. The device of claim 21, wherein the diode protection circuit is a flip chip diode array component mounted on the printed circuit board.

26. The device of claim 22, wherein the medical device contact regions of the printed circuit board are wire bonded to corresponding pads of the medical device circuit assembly.

27. The device of claim 22, wherein the at least one electrically conductive pin is directly connected to the at least one conductive pin contact region of the printed circuit board.

28. The device of claim 27, wherein the at least one electrically conductive pin is aligned with the at least one conductive pin contact region of the printed circuit board.

29. The device of claim 21, wherein the implantable medical device is selected from one of a pacemaker, a brain stimulator, a defibrillator, a pacemaker/cardioverter/defibrillator, a cardioverter/defibrillator, a neurostimulator, a muscle stimulator, a gastric stimulator, an implantable monitor, and a drug pump.

* * * * *